US006050265A

United States Patent [19]
Richardson

[11] Patent Number: 6,050,265
[45] Date of Patent: Apr. 18, 2000

[54] THERAPEUTIC PILLOWS

[76] Inventor: Albert Lee Richardson, 1108 Wren Dr., Hanford, Calif. 93230

[21] Appl. No.: 09/103,132

[22] Filed: Jun. 23, 1998

[51] Int. Cl.[7] .................................................. B11G 5/125
[52] U.S. Cl. .................................... 128/845; 5/632; 5/636
[58] Field of Search .................................... 128/845, 846; 5/625, 632, 636, 637, 461, 646

[56] References Cited

U.S. PATENT DOCUMENTS

| | | | |
|---|---|---|---|
| 2,800,897 | 7/1957 | Ross | 5/632 |
| 3,061,844 | 11/1962 | Coursey | 5/640 |
| 4,773,107 | 9/1988 | Josefek | 5/636 |
| 4,876,755 | 10/1989 | Parrish | 5/636 |
| 5,193,236 | 3/1993 | Komuro | 601/15 |
| 5,647,076 | 7/1997 | Gearhart | 5/632 |

*Primary Examiner*—Michael A. Brown
*Attorney, Agent, or Firm*—Michael I. Kroll

[57] ABSTRACT

A therapeutic pillow is fabricated in one or more separate sections that may be attached to each other, may be filled to suit the user, and may incorporate the use of heating and message devices as well as a plurality of small magnets.

2 Claims, 11 Drawing Sheets

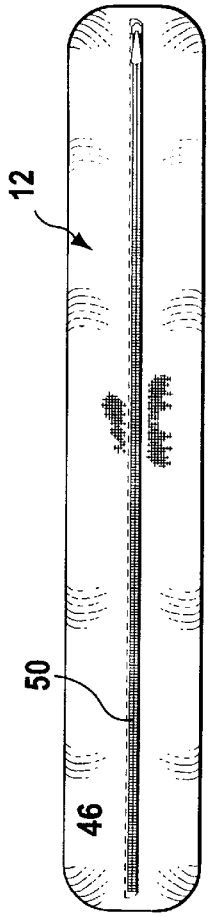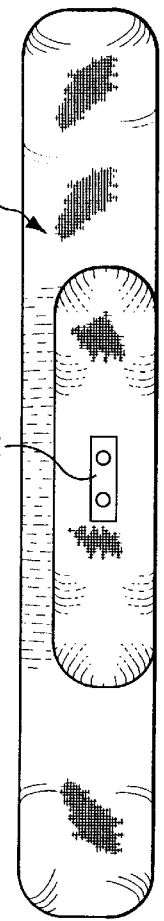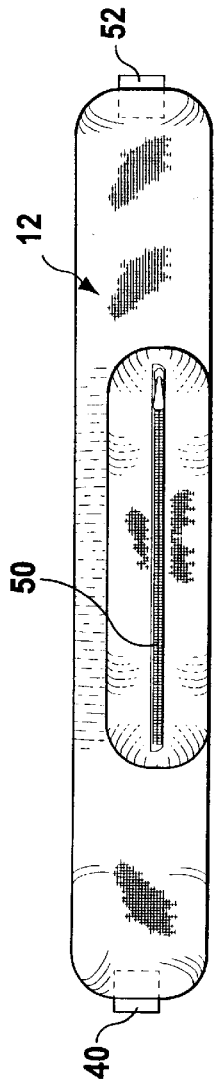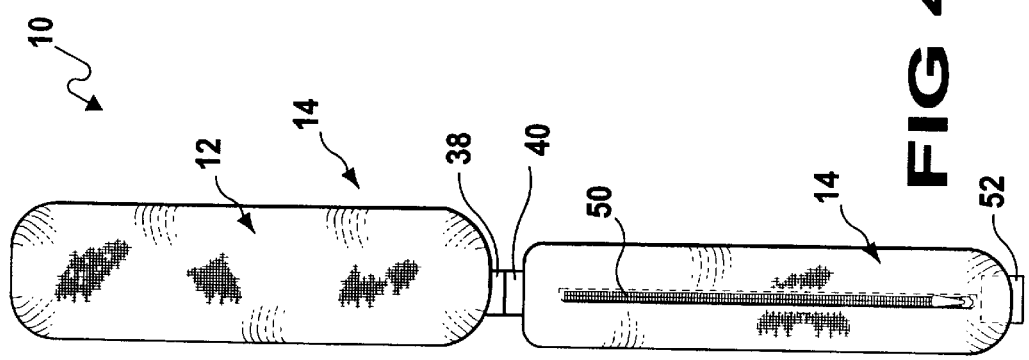

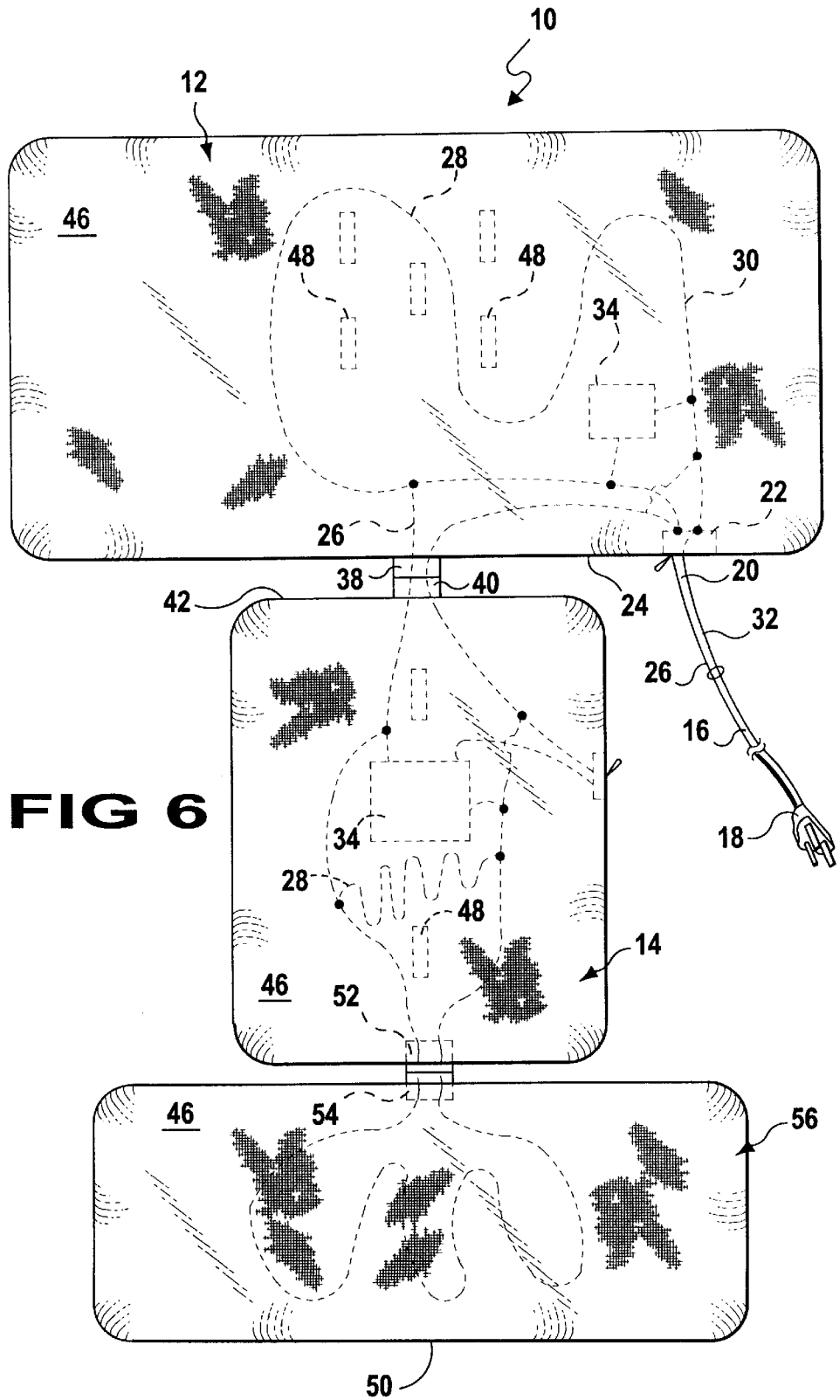

THERAPEUTIC PILLOWS

BACKGROUND OF THE INVENTION

1. Field of the Invention

The present invention relates generally to pillows and, more specifically, to a pillow which supports the head, neck and spinal column, as needed.

2. Description of the Prior Art

There are numerous pillows designed to provide for head and neck support. Typical of these pillows is U.S. Pat. No. 4,966,734 issued to Rowe on Mar. 5, 1991.

Another pillow patent was issued to Wood on Apr. 19, 1966 as Des. 204,443. Yet another U.S. Pat. No. Des. 264,557 was issued to Haase on May 18, 1982.

U.S. Pat. No. 4,996,734

Inventor: Shelba D. Rowe

Issued: Mar. 5, 1991

An improved pillow having a head supporting portion and a neck supporting portion. The neck supporting portion having a firmness greater than the head supporting portion. The neck supporting portion is of lesser transverse dimension than the head supporting portion to allow freedom from interference of the pillow with the sleeper's jaw and mouth. In an alternate version, the pillow includes two reversible neck supporting portions of different firmness.

U.S. Pat. No. Des 204,443

Inventor: Nadean Wood

Issued: Apr. 19, 1966

This United States Patent discloses an ornamental design for a pillow as illustrated in the drawings of the patent U.S. Pat. No. Des 348,583

Inventor: Linda D. Rubin

Issued: Jul. 12, 1994

This United States Patent discloses an ornamental design for a pillow as illustrated in the drawings of the patent U.S. Pat. No. Des 264,507

Inventor: Evangline M. Haase

Issued: May 18, 1982

This United States Patent discloses an ornamental design for a posture pillow as illustrated in the drawings of the patent While these pillows may be suitable for the purposes for which they were designed, they would not be as suitable for the purposes of the present invention, as hereinafter described.

SUMMARY OF THE PRESENT INVENTION

A primary object of the present invention is to provide a pillow that will support the head, neck and spinal column of an individual.

Another object of the present invention is to provide a pillow where the density or hardness of the pillow can be adjusted by the user thereof by insertion or removal of the padding material.

Yet another object of the present invention is to provide a pillow with a massaging capability while supporting the head, neck and spinal column.

Still yet another object of the present invention is to provide a pillow with a heating capability while supporting the head, neck and spinal column.

Yet another object of the present invention is to provide a pillow containing a plurality of magnets which may be disposed around the head area, or located in a vertical position in line with the spinal column while supporting the head, neck and spinal column.

Additional objects of the present invention will appear as the description proceeds.

The present invention overcomes the shortcomings of the prior art by providing a pillow which supports the head, neck, spinal column and alternately the hips, wherein the pillow can be unitary in design or a multiple sectioned pillow wherein one or more of the sections may be used as desired by an individual.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING

In order that the invention may be more fully understood, it will now be described, by way of example, with reference to the accompanying drawing in which:

FIG. 2 is a top end view in elevation of the head section shown in FIG. 1 showing the re-closable opening;

FIG. 3 is a bottom end view in elevation of the head section shown in FIG. 1 showing the first electrical socket device disposed thereon;

FIG. 4 is a side view in elevation of head and back sections of the preferred embodiment of a therapeutic pillow as shown in FIG. 1;

FIG. 5 is a side view in elevation of the back section of the therapeutic pillow showing the re-closable opening disposed on one edge thereof;

FIG. 6 is a top plan view of the head, back and hip sections connected together of a therapeutic pillow, according to the principles of the present invention;

DESCRIPTION OF THE PREFERRED EMBODIMENTS

Figure 1:
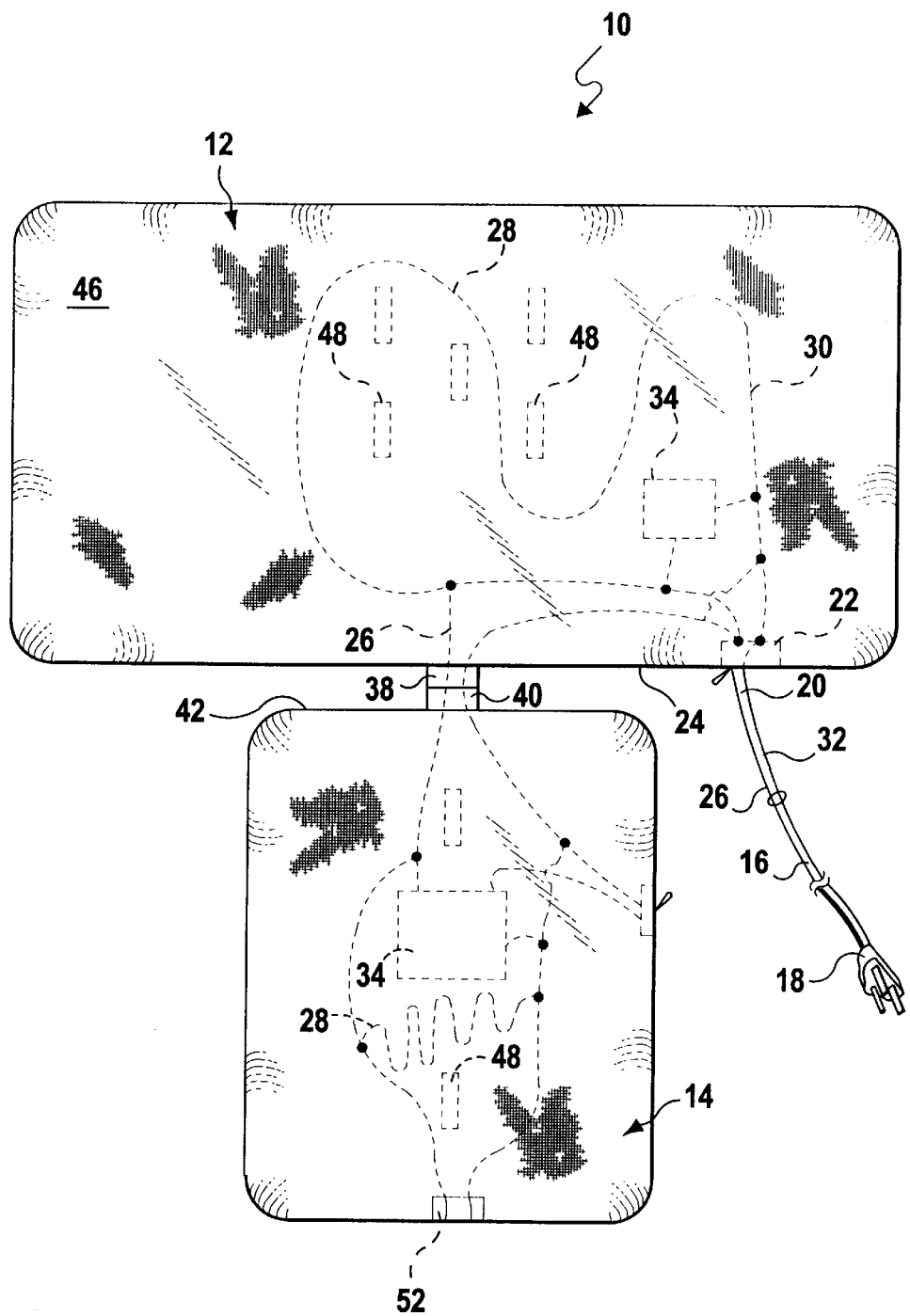
FIG. 1 is a top plan view of the head and back sections of a therapeutic pillow, connected together, according to the principles of the present invention.

Turning now descriptively to the drawings, in which similar reference characters denote similar elements throughout the several views, the Figures illustrate a multiple sectioned pillow wherein one or more of the sections may be used as desired by a individual. With regard to the reference numerals used, the following numbering is used throughout the various drawing figures.

| | |
|---|---|
| 10 | Therapeutic pillow |
| 12 | therapeutic pillow head section |
| 14 | therapeutic pillow back section |
| 16 | electrical line cord |
| 18 | electrical line cord plug |
| 20 | electrical line cord other end |
| 22 | toggle switch |
| 24 | one edge of therapeutic pillow head section |
| 26 | electrical line cord plug ground |
| 28 | resistance heating apparatus |
| 30 | other end of heating apparatus |
| 32 | high side |
| 34 | vibrating apparatus |
| 36 | switch |
| 38 | therapeutic pillow head section electrical socket |
| 40 | therapeutic pillow back section electrical plug |
| 42 | one end of therapeutic pillow back section |
| 44 | therapeutic pillow head section re-closable opening |
| 46 | therapeutic pillow padding material |
| 48 | magnets |
| 50 | therapeutic pillow back section re-closable opening |
| 52 | therapeutic pillow back section electrical socket |
| 54 | therapeutic pillow hip section electrical plug |
| 56 | therapeutic pillow hip section |
| 58 | pillow |
| 60 | hook and loop fastener |
| 110 | therapeutic pillow |
| 210 | therapeutic pillow |

Referring now to the figures, and particularly to FIG. 1 there is shown a therapeutic pillow 10, which is seen to include a head section 12 and a back section 14. The head section 12 includes a line cord 16 having a plug 18 disposed on one distal end thereof for insertion into a conventional line voltage socket, not shown. The other end 20 is connected to a line toggle switch 22 disposed proximate one edge 24 of the head section 12.

Switch 22, when turned ON is connected to the return or ground 28 of a resistance heating apparatus 28. The other end 30 of the heating apparatus 28 is connected to the high side 32 of the input line voltage. A vibrating apparatus 34 may also be connected across the input line voltage to be activated by the switch 22 or it may incorporate a separate switch, (see FIG. 10).

FIG. 2 is a top end view in elevation of the head section shown in FIG. 1 showing the re-closable opening 50, e.g. a zipper or velcro, which is used to insert or remove various types of padding material 46, that may include a plurality of small magnets 48, the heating apparatus 28 and/or the vibrating apparatus 34.

The head section 12 also is seen to include a socket 38 (see FIG. 3), which is adapted to mate and cooperate with a plug 40 disposed on one end 42 of the back section 14 of the pillow 10.

FIG. 4 is a side view in elevation of head section 12 and back section 14 of the preferred embodiment of the invention connected together by the cooperating socket 38 and the plug 40.

Referring now to FIG. 5, which shows a side view in elevation of the back section 14 of the therapeutic pillow showing the re-closable opening 50 disposed on one edge thereof suitable for insertion and removal of the padding material 46, which may include a plurality of small magnets 48, the heating apparatus 28 and/or the vibrating apparatus 34, as set forth in the description of the head section 12 of the therapeutic pillow 10.

Figure 7:
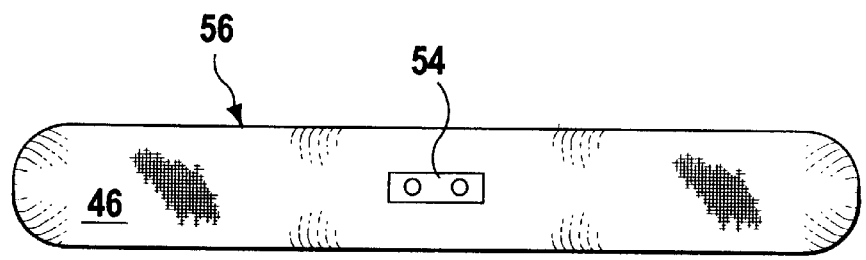
FIG. 7 is a top view in elevation of the hip section shown in FIG. 6.
Figure 8:
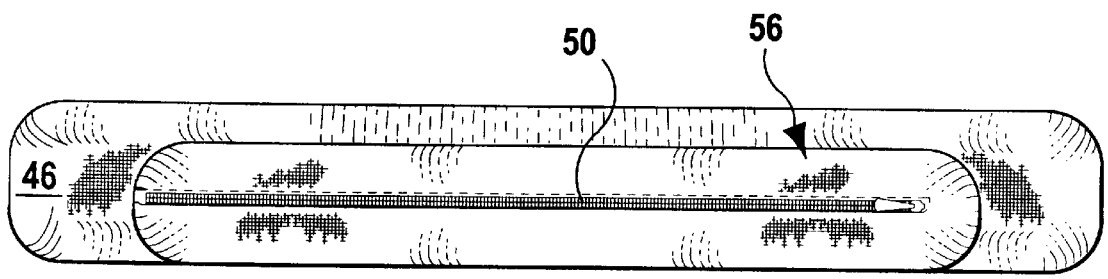
FIG. 8 is a end view in elevation of the hip section showing the re-closable opening means disposed thereon.

Referring now to FIGS. 6-8, it can be seen that the opposite end from plug 40 of the back section 14 includes a socket 52 adapted to cooperate with a plug 54 disposed on one end of the hip section 56, which is fabricated in a manner similar to head section 12 and back section 14 of the therapeutic pillow 10 and may include padding material 46, which may include a plurality of small magnets 48, the heating apparatus 28 and/or the vibrating apparatus 34, as set forth earlier, and also includes a re-closable opening 50 disposed on one edge thereof.

Figure 9:
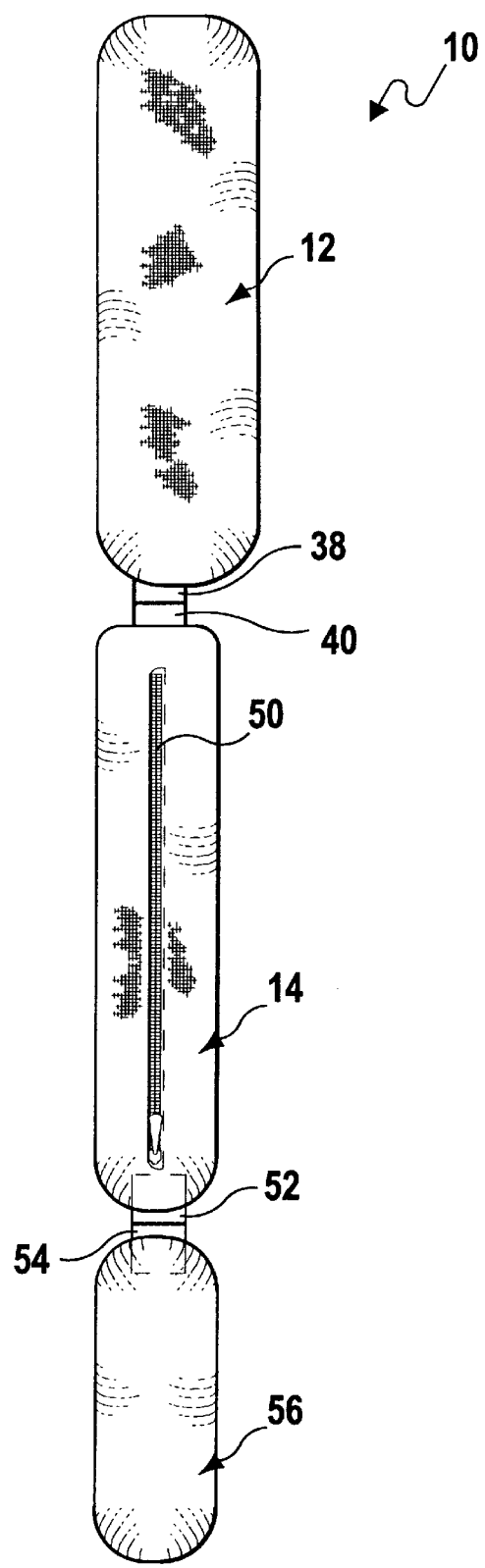
FIG. 9 is the other side view in elevation of the head, back and hip sections connected together as shown in FIG. 6.

FIG. 9 is a side view in elevation of the head section 12, the back section 14 and the hip section 56 connected together as shown in FIG. 6. Plug 54 carries the current into hip section 56, when it is connected to the socket 52 in the same manner that power is obtained in back section 12, when plug 40 is connected to socket 30 disposed on head section 12 of the therapeutic pillow 10.

Figure 10:
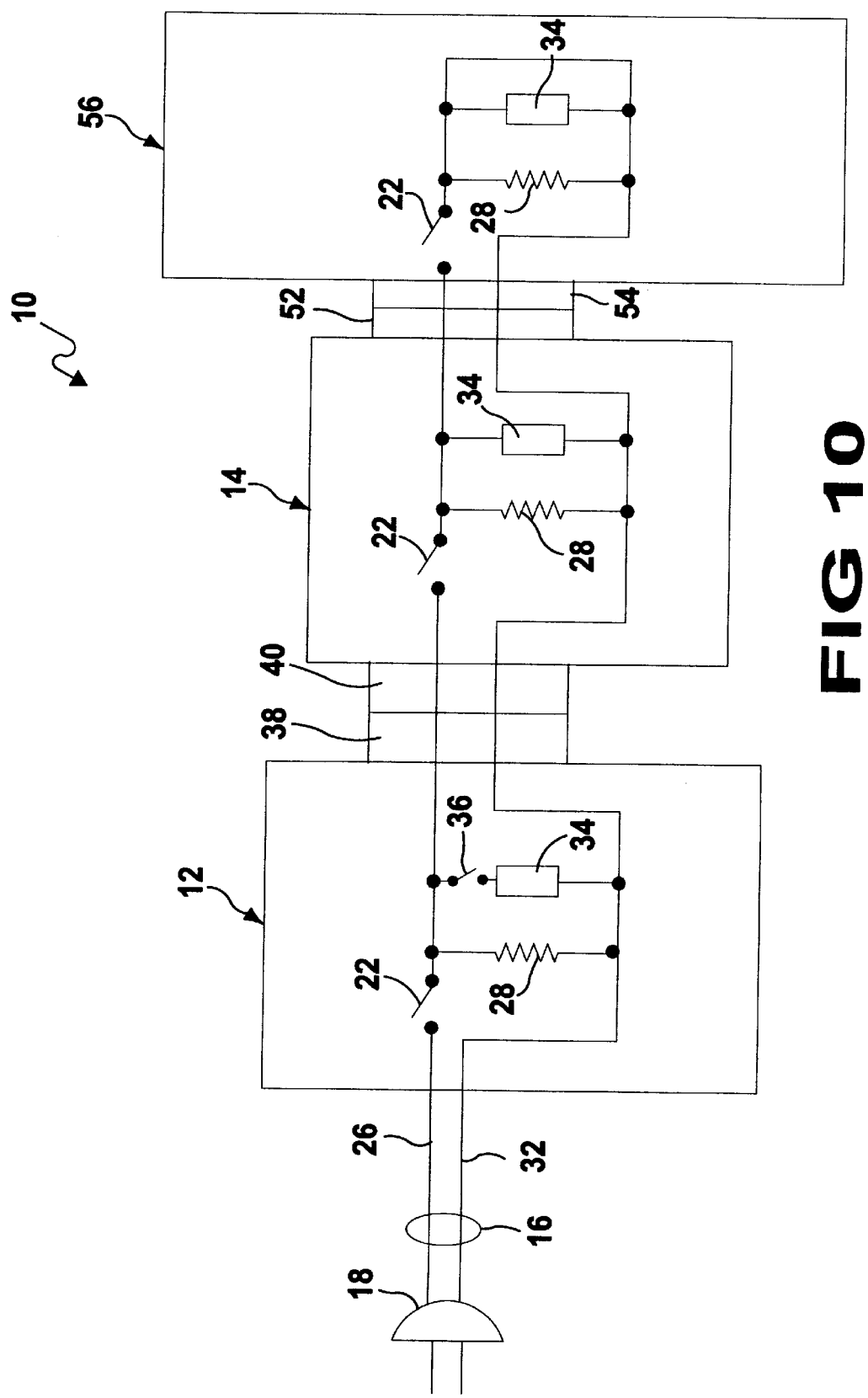
FIG. 10 is an electrical circuit diagram of the preferred embodiment of the invention.

FIG. 10 is an electrical circuit diagram of the preferred embodiment of the invention showing one manner of interconnecting the various components located in the three sections of the therapeutic pillow 10.

Figure 1A:
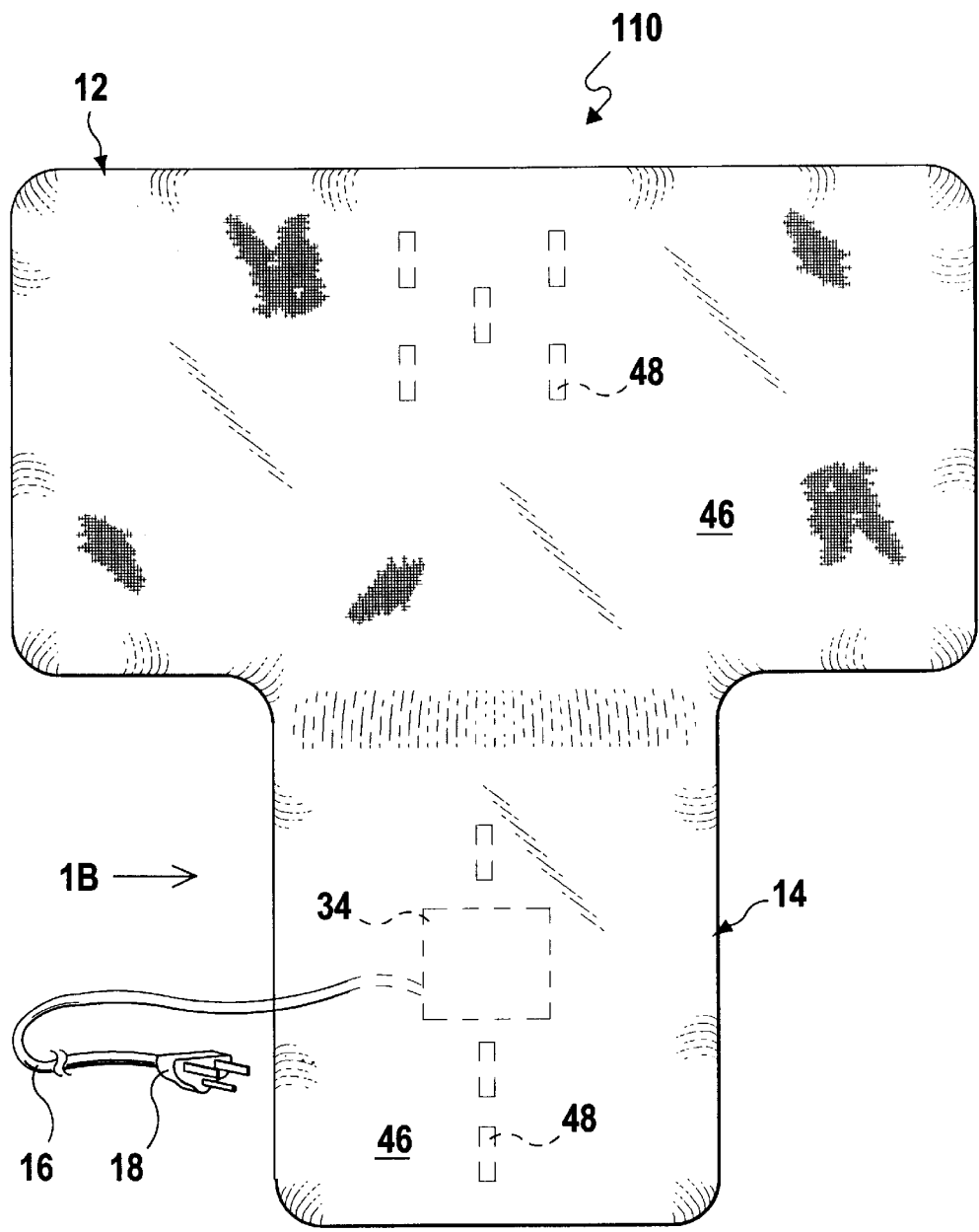
FIG. 1A is a top plan view of the one piece head and back sections of an alternate embodiment of a therapeutic pillow with various types of padding materials disposed therein.
Figure 1D:
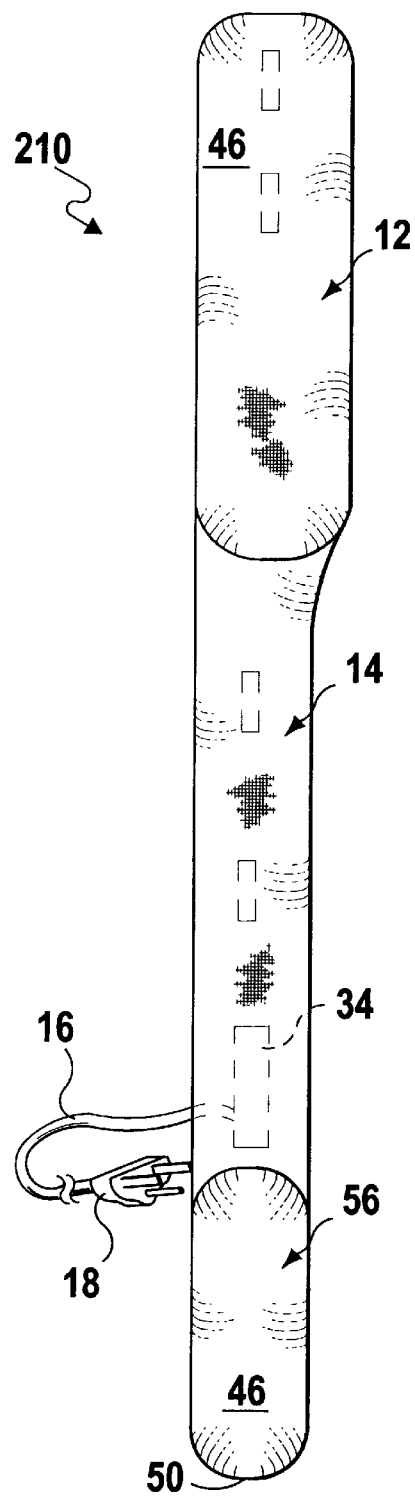
FIG. 1D is a side view in elevation of the alternate embodiment shown in FIG. 1C.
Figure 1B:
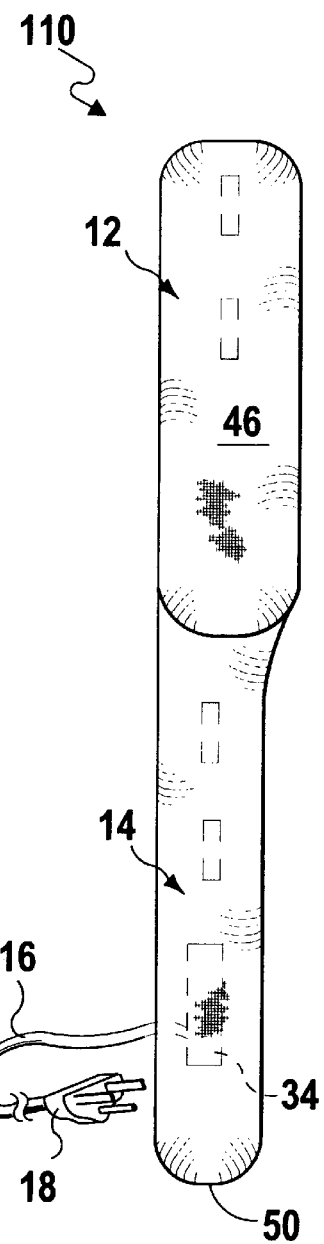
FIG. 1B is a side view in elevation of the embodiment shown in FIG. 1A.
Figure 1C:
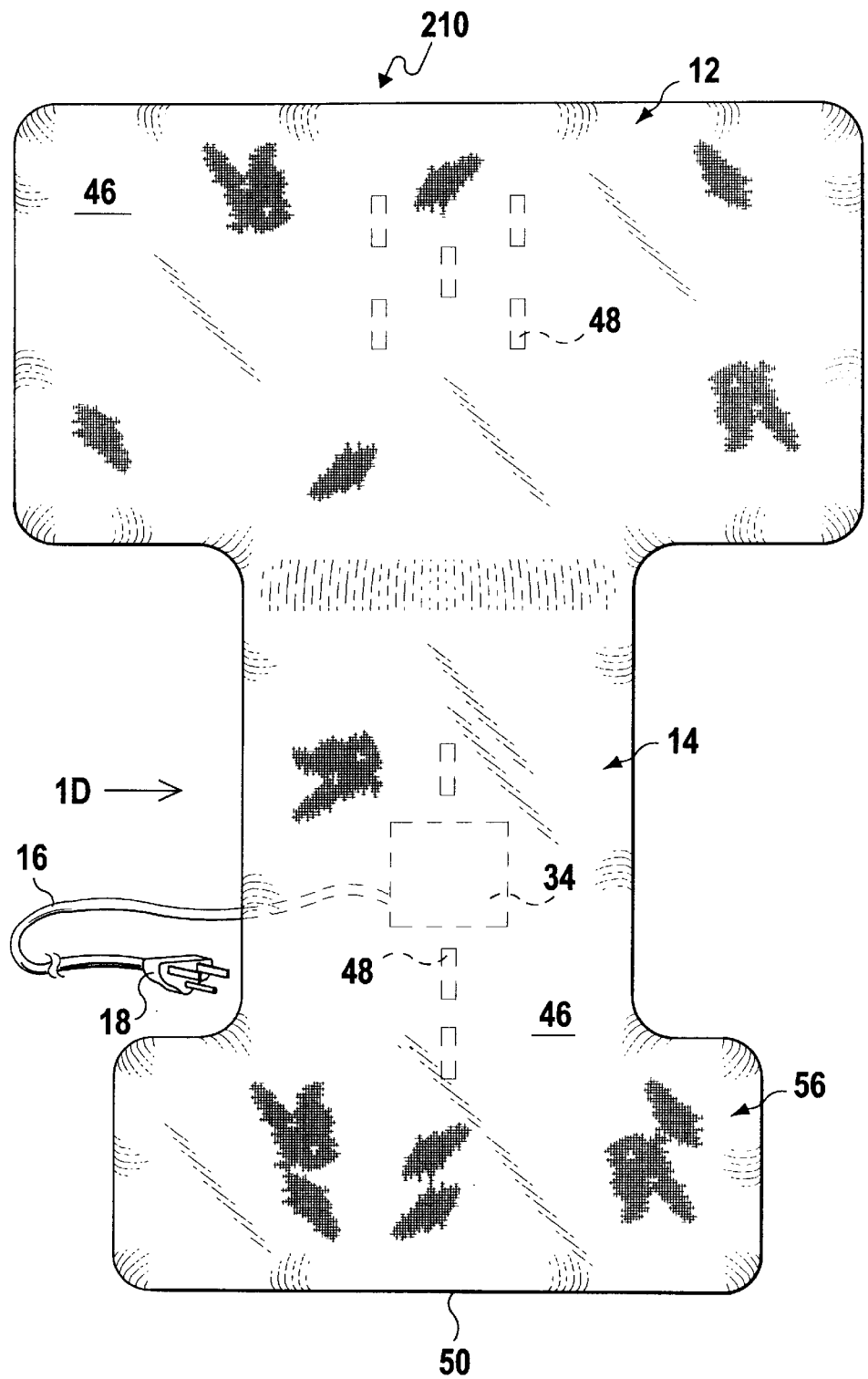
FIG. 1C is a top plan view of the one piece head, back and hip sections of another alternative embodiment of a therapeutic pillow with various types of padding materials disposed therein.

The alternative embodiments shown in FIGS. 1A and 1C are similar to the embodiments shown in FIGS. 1-10 except the alternative embodiments are fabricated as unitary assemblies.

Referring now to FIG. 1A there is shown an alternate embodiment wherein the head section 12 and back section 14 are fabricated as a unitary therapeutic pillow 110.

FIG. 1B is a side view in elevation, taken from FIG. 1A as indicated, showing the head section 12 and back section 14 of the alternate embodiment therapeutic pillow 110 having a re-closable opening 50 disposed on one end.

FIG. 1C shows another alternate embodiment wherein the head section 12, back section 14 and hip section 56 are fabricated as a unitary therapeutic pillow 210.

FIG. 1D is a side view in elevation, taken from FIG. 1C as indicated, showing the head section 12, back section 14, and hip section 56 of the other alternate embodiment of the therapeutic pillow 210 having a re-closable opening 50 disposed on one end thereby providing means for removing and inserting padding material 46 that may contain small magnets 48, and/or a vibrating apparatus 34, as well as heating element 28.

Figure 1E:
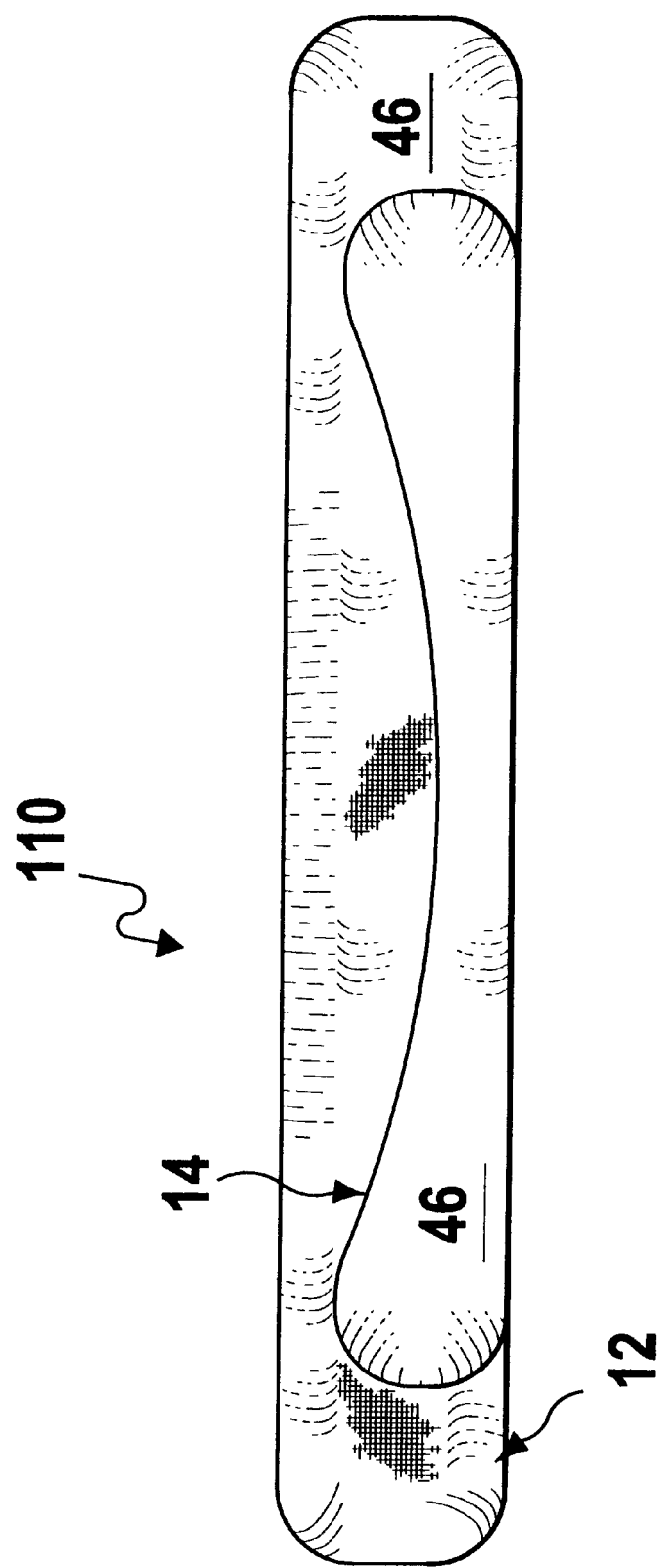
FIG. 1E is an end view of another embodiment of the back section shown in FIG. 1A wherein the shape of the back portion is concave relative to the head portion of the embodiment shown in FIG. 1A.

FIG. 1E is an end view in elevation of the alternate embodiment 110 wherein the back section 14 has a concave contour in relation to head section 12.

Figure 1F:
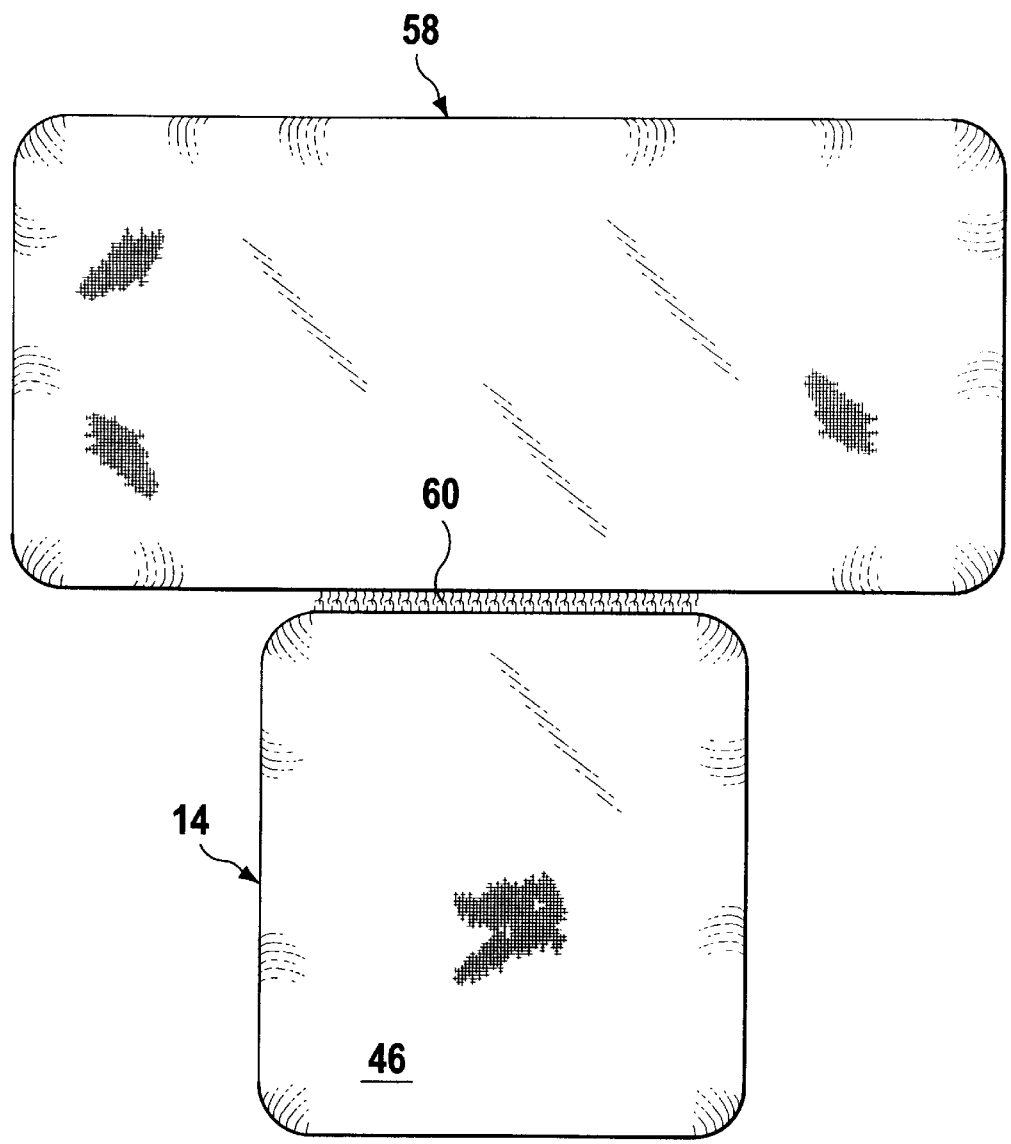
FIG. 1F is a top plan view of a pillow wherein a length of hook and loop fastener is used to connect the back support section of the present invention to an existing pillow.

FIG. 1F is a top plan view showing that the back section 14 can be attached by means of hook and loop fastener to an existing pillow or by hooks, clamps, strips, or any method which would convert an existing pillow into a pillow providing head, back and spinal column support.

Hereinbefore has been disclosed a therapeutic pillow that may be used as a complete unit or only two sections may be used if desired.

It will be understood that various changes in the details, materials, arrangements of parts and operating conditions which have been herein described and illustrated in order to explain the nature of the invention may be made, by those skilled in the art, within the principles and scope of the instant invention.

Having thus set forth the nature of the invention, what is claimed is:

1. A therapeutic pillow comprising:
   a) a head section containing padding material and a plurality of magnets, resistance heating apparatus, and vibrating apparatus, said head section further including a re-closable opening for inserting or removing padding material, magnets, heating apparatus, and vibrating apparatus;
   b) a back section connected to said head section containing padding material, a plurality of magnets, resistance heating apparatus, and vibrating apparatus; and
   c) means for supplying electric power to said resistance heating and vibrating apparatus comprising a line cord for connection to a source of electrical power, a toggle switch mounted on said pillow for turning on said heating and vibrating apparatus, and electrical wiring extending from within said head section to within said back section for activating the heating and vibrating apparatus in both of said head and back sections.

2. A one piece therapeutic pillow comprising:
   a) a head section having flat top and bottom surfaces containing padding material and a plurality of magnets;
   b) a hip section having flat top and bottom surfaces containing padding material and at least one magnet;
   c) a back section having flat top and bottom surfaces joining said head and hip sections, said back section narrower that either of said head and hip sections, containing padding material, at least one magnet, and a vibrator; and
   d) means for supplying electrical power to said vibrator.

* * * * *